United States Patent [19]

Okawa et al.

[11] Patent Number: 5,364,896
[45] Date of Patent: Nov. 15, 1994

[54] METHOD FOR PREPARING SILICA FILLED ORGANOSILOXANE COMPOSITIONS

[75] Inventors: Tadashi Okawa; Shuji Yamada, both of Chiba, Japan

[73] Assignee: Dow Corning Toray Silicone Co., Ltd, Tokyo, Japan

[21] Appl. No.: 974,053

[22] Filed: Nov. 10, 1992

[30] Foreign Application Priority Data

Nov. 26, 1991 [JP] Japan .................. 3-336078

[51] Int. Cl.$^5$ ................................. C08K 5/54
[52] U.S. Cl. .................... 524/266; 524/730
[58] Field of Search ............... 524/730, 266; 556/453, 556/456, 459

[56] References Cited

U.S. PATENT DOCUMENTS

| | | | |
|---|---|---|---|
| 2,954,357 | 9/1960 | Fekete | 524/266 |
| 3,133,110 | 5/1964 | Morehouse et al. | 556/453 |
| 3,231,575 | 1/1966 | Selin | 556/459 |
| 3,322,360 | 12/1965 | Prescott et al. | 260/290 |
| 3,337,497 | 8/1967 | Bostick | 556/459 |
| 3,532,731 | 10/1970 | Hittmair et al. | 556/453 |
| 3,542,834 | 11/1970 | Alsgaard | 556/459 |
| 4,052,357 | 10/1977 | Marinik | 524/266 |
| 4,515,976 | 5/1985 | Preiner et al. | 556/453 |

FOREIGN PATENT DOCUMENTS 500798 12/1951 Belgium .
1422112 9/1964 France .

*Primary Examiner*—Ralph H. Dean
*Attorney, Agent, or Firm*—Robert Spector

[57] ABSTRACT

The triorganosiloxydiphenylsilanols of the present invention are novel silicone compounds that are useful as plasticizers for silicone rubbers. The present invention also relates to a method for preparing these compounds in high yield and purity and a method for preparing filled curable organosiloxane compositions using the present compounds as plasticizers.

3 Claims, 2 Drawing Sheets

METHOD FOR PREPARING SILICA FILLED ORGANOSILOXANE COMPOSITIONS

BACKGROUND OF THE INVENTION

1. Field of the Invention

The present invention relates to triorganosiloxydiphenylsilanols, which are novel organosilicone compounds useful as plasticizers for silicone rubbers. The present invention also relates to a method for the preparation of said triorganosiloxydiphenylsilanol and to a method for preparing filled organosiloxane compositions using these compounds.

2. Background Information

Silicone rubbers are used in a variety of applications because of their high resistance to heat and cold. Various types of inorganic fillers are typically blended into the polyorganosiloxanes present in the curable compositions used to prepare these rubbers to improve the physical properties of the cured rubber. However, as a result of a pseudo-crosslinking that results from interactions between the polyorganosiloxane and the inorganic filler, the blendability or workability during blending of the silicone rubber composition deteriorates with the passage of time In order to prevent this pseudo-crosslinking, curable organosiloxane compositions have heretofore been prepared using a silanol-containing low molecular weight organosilicon compound as a plasticizer for the silicone rubber. Examples of these plasticizers include but are not limited to diphenylsilanediol and oligomeric organosiloxanes such as alpha,omega-dihydroxydimethylsiloxanes alpha,omega-dihydroxymethylvinylsiloxanes, and alpha,omega-dihydroxymethylphenylsiloxanes.

The oligomeric organosiloxanes have not performed satisfactorily as silicone rubber plasticizers. Diphenylsilanediol performs well as a plasticizer, however its use is associated with the development of white spots on the surface of the cured silicone rubber.

The present inventors developed the present invention as the result of extensive research directed at solving the aforementioned problems associated with prior art plasticizers in curable organosiloxane compositions.

SUMMARY OF THE INVENTION

One objective of the present invention is to provide a novel class of organosilicon compounds, namely triorganosiloxydiphenylsilanols, which are useful as plasticizers for use in curable organosiloxane compositions that yield rubbers upon curing. A second objective of the present invention is to provide the a method for preparing these triorganosiloxydiphenylsilanols. Another objective of this invention is to provide a method for treating silica and other fillers for organosiloxane compositions using these compounds.

DETAILED DESCRIPTION OF THE INVENTION

The present invention provides triorganosiloxydiphenylsilanols of the general formula

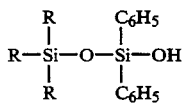

in which each R is individually selected from group consisting of substituted and unsubstituted monovalent hydrocarbon radicals and $C_6H_5$ represents the phenyl radical.

This invention also provides a method for preparing these triorganosiloxydiphenylsilanols.

Figure 1:
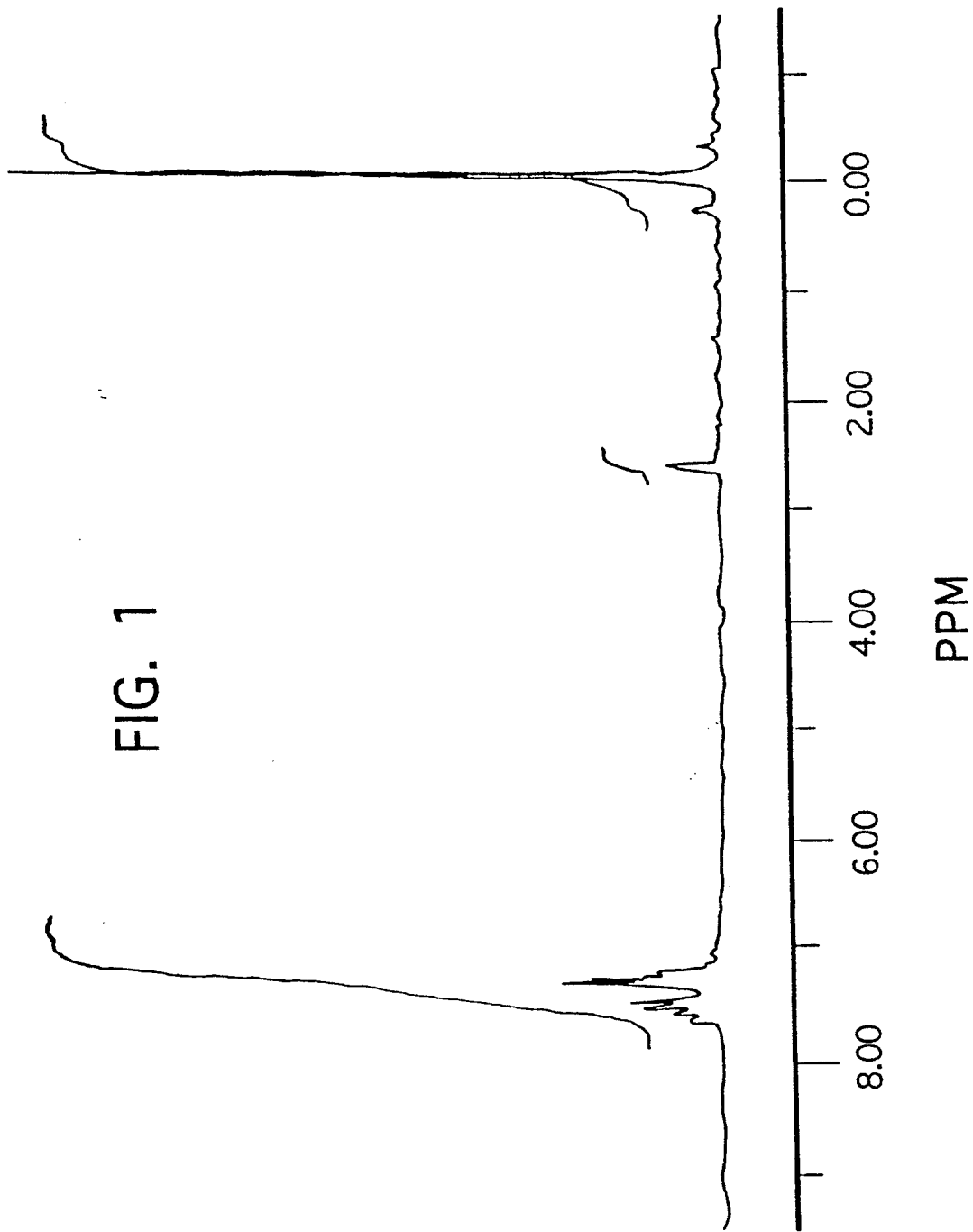
FIG. 1 depicts the $^1H$ nuclear magnetic resonance analytic spectrum for the trimethylsiloxydiphenylsilanol prepared in Example 1.
Figure 2:
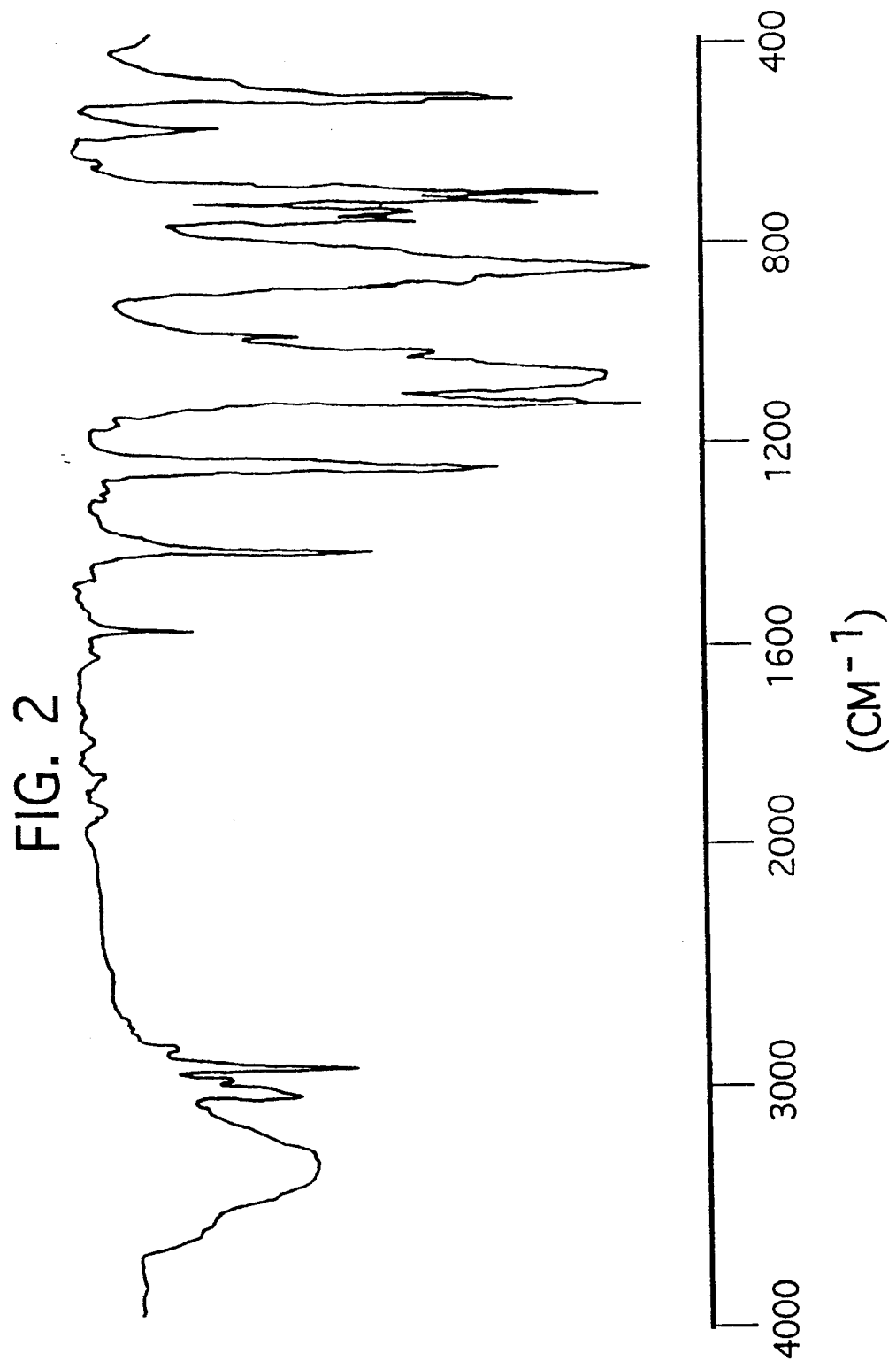
FIG. 2 depicts the infrared spectrum for the trimethylsiloxydiphenylsilanol prepared in Example 1.

In accordance with the present method a triorganosilanol and a diphenyldihalosilane are reacted to yield a triorganosiloxydiphenylhalosilane of the general formula

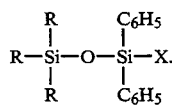

This triorganosiloxydiphenylhalosilane is then hydrolyzed and the resultant triorganosiloxydiphenylsilanol is isolated from the reaction mixture. The halogen atom repented by X can be fluorine chlorine, bromine or iodine.

The present compounds are represented by the general formula

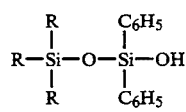

The substituted and unsubstituted monovalent hydrocarbon represented by R include but are not limited to alkyl groups such methyl, ethyl, propyl, butyl, pentyl, and hexyl; alkenyl radicals such as vinyl, allyl, butenyl, hexenyl, and isopropenyl; aryl radicals groups such as phenyl, tolyl, and xylyl; aralkyl radicals such as benzyl, and phenethyl; and halogen-substituted alkyl groups such as chloroethyl and 3,3,3-trifluoropropyl. The hydrocarbon radicals represented by each of the R substituents can be identical or different.

Each of the radicals represented by R is preferably methyl based on considerations of ease of synthesis, ease of starting material acquisition, economics, and the excellent properties of these compounds as silicone rubber plasticizers.

Because the triorganosiloxydiphenylsilanols of the present invention are, like diphenylsilanediol, silanol-containing organosilicon compounds, addition of the present compounds to a mixture of a curable polyorganosiloxane and an inorganic filler improves the blendability or compoundability of these ingredients and improves the storage stability of the resulting silicone rubber composition. But in addition, because it is much more compatible with polyorganosiloxanes than diphenylsilanediol, it also offers the highly desirable feature of not producing white spots on the surface of the silicone rubber product.

Examples of methods for preparing the triorganosiloxydiphenylsilanols of the present invention include but are not limited to (a) the reaction of diphenylsilanediol and triorganohalosilane; (b) the reaction of a hexaorganodisilazane, a diphenyldihalosilane, and water; and (c) the reaction of a triorganosilanol and a diphenyldihalosilane to yield a triorganosiloxydiphenylhalosilane, followed by hydrolysis of this triorganosiloxydiphenylhalosilane. Methods (a) and (b) suffer from low triorganosiloxydiphenylsilanol yields. Another problem with these two methods is that the purity of the triorganosiloxydiphenylsilanol cannot be increased due to the production of large amounts of by-products with very similar physical properties such as boiling point and melting point.

Because of the aforementioned shortcomings, the preferred method for obtaining the desired triorganosiloxydiphenylsilanol in high yield and purity comprises reacting a triorganosilanol and a diphenyldihalosilane to yield the corresponding triorganosiloxydiphenylhalosilane, followed by hydrolysis of this halosilane to the corresponding silanol.

The preferred embodiment of the present preparative method will now be considered in detail. During the first step of this method a triorganosiloxy-diphenylhalosilane of the general formula

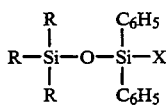

is synthesized by the reaction of triorganosilanol and diphenyldihalosilane. The second step involves a hydrolysis of the resultant triorganosiloxydiphenylhalosilane. R in this formula is a hydrocarbon radical as previously defined and X represents a halogen atom, specifically fluorine, chlorine, bromine or iodine.

The triorganosilanol used in the preferred method has the general formula

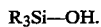

The triorganosilanol can be synthesized by known methods, which include but are not limited to careful hydrolysis of a hydrolyzable organosilicon compound such as a triorganohalosilane, triorgano(organocarboxy)silane, or hexaorganodisilazane.

The diphenyldihalosilane used as a reactant in the present method exhibits the general formula.

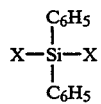

where X is a halogen atom as previously defined. These diphenyldihalosilanes are available commercially.

While the molar ratio between the triorganosilanol and the diphenyldihalosilane is not specifically restricted, this ratio is preferably within the range of from 1.0 to 10, most preferably from 1.2 to 5. The basis for these preferences is the important effect of this ratio on the relative amounts of the desired triorganosiloxydiphenylhalosilane and the corresponding bis(triorganosiloxy)diphenylsilane produced as an undesirable by-product of the reaction. The production of bis(triorganosiloxy)diphenylsilane increases and the reaction selectivity declines when the diphenyldihalosilane: triorganosilanol molar ratio falls below 1.0. On the other hand, while the selectivly of the reaction continues to improve at diphenyldihalosilane/triorganosilanol molar ratios in excess of 10, the amount of unreacted diphenyldihalosilane is also increased, which impairs the economics of the reaction.

The first step of the present method is a dehydrochlorination reaction that proceeds readily at room temperature. However, in order to inhibit condensation reactions between silanol groups and in order to prevent polyorganosiloxane chain equilibration reactions, it is preferable to include in the reaction mixture a base that will react with the hydrogen halide HX formed as a by-product of the reaction. Examples of suitable bases include but are not limited to ammonia and organic amines.

The first step of the present method can be conducted in a solventless system, however, when a base is present the reaction is preferably conducted in the presence of a suitable aprotic solvent due to the generation of large amounts of salt from the hydrogen halide/base reaction. Suitable aprotic solvents include but are not limited to liquid aromatic hydrocarbons such as benzene, toluene and xylene; liquid aliphatic hydrocarbons such as hexane and heptane; liquid ethers such as tetrahydrofuran and diethyl ether; liquid ketones such as acetone and methyl ethyl ketone; liquid esters such as ethyl acetate and butyl acetate; chlorinated hydrocarbons such as trichloroethane and chloroform; and other organic liquid such as dimethyl sulfoxide and dimethylformamide.

The second step of the preferred method is a hydrolysis of the triorganosiloxydiphenylhalosilane to yield the desired triorganosiloxydiphenylsilanol. While this reaction can be conducted in the absence of solvents, it is preferably run in the presence of a suitable solvent. The aprotic solvents listed ill the preceding section of this specification are also suitable for the hydrolysis reaction. When the molar ratio of dipenyldihalosilane to triorganosilanol is greater than 1.0, the use of a non-polar solvent such as hexane or toluene as the aprotic solvent can facilitate separation and purification of the desired product. Under such circumstances, the unreacted diphenyldihalosilane is hydrolyzed to the corresponding diphenylsilanediol, which is insoluble in the aprotic solvent and precipitates. While the hydrolysis reaction will proceed even at room temperature, the reaction rate is increased by heating the reaction mixture. The reaction mixture preferably contains a basic compound such an acetate, carbonate or bicarbonate of potassium or sodium to react with the hydrogen halide formed as a by-product of the hydrolysis reaction.

The triorganosiloxydiphenylsilanols of the present invention exhibit excellent activity when used as plasticizers for filled silicone rubber compositions. In accordance with a preferred embodiment of the present method for preparing these compositions, 100 weight parts of a curable organosiloxane are blended with from 5 to 100 weight parts of an inorganic filler and an amount of curing agent sufficient to induce curing of the polyorganosiloxane.

Suitable inorganic fillers for use in the present method for preparing filled organosiloxane compositions include but are not limited to reinforcing fillers such as precipitated silica, fumed silica, calcined silica and fumed titanium oxide; extending fillers such as powdered quartz, diatomaceous earth, asbestos, aluminosilicic acid, iron oxide, zinc oxide, and calcium carbonate. Suitable fillers include any of these reinforcing or extending fillers that have been previously treated with organosilicon compounds such as hexamethyldisilazane, trimethylchlorosilane, and polymethylhydrogensiloxanes.

In order to inhibit the pseudo-crosslinking due to interactions between such inorganic fillers and silicone polymers, the present triorganosiloxydiphenylsilanols are preferably added at concentrations of from 0.05 to 20 weight parts per 100 weight parts of curable polyorganosiloxane(s). When the concentration of triorganosiloxydiphenylsilanol is less than 0.05 weight parts, pseudo-crosslinking will still occur in the curable organosiloxane composition and the compoundability or blendability of the composition will deteriorate. Triorganosiloxydiphenylsilanol concentrations above 20 weight parts are excessive and therefore economically disadvantageous.

EXAMPLES

The present invention will now be explained in detail using illustrative examples, The methods described in JIS K 6301 were used to measure reported physical properties of the silicone rubber molded sheet, such as hardness, tensile strength, tear strength and elongation. The presence or absence of white spots on the surface of the cure silicone rubber molded sheet was determined by examining the sheet one week after it had been cured and allowed to remain at room temperature.

Example 1

The following were ingredients were introduced into a stirrer-equipped four-neck flask: 164.8 g (651.2 mmol) diphenyldichlorosilane and 300 mL tetrahydrofuran. The resultant mixture was stirred at room temperature while a mixture of 60 g (542.7 mmol) of 81.4% pure trimethylsilanol and 65.9 g (651.2 mmol) of triethylamine was added dropwise. Stirring at room temperature was continued for an additional hour following completion of the addition, at which time the salt formed as a by-product of the reaction was removed by filtration. The filtrate was then distilled under reduced pressure to yield 118.7 g of a fraction boiling at 136.5° C.-142° C. under of 2 mm Hg, equivalent to a 71.4% yield of trimethylsiloxydiphenylchlorosilane. Analysis of this product by gas chromatography (GLC), nuclear magnetic resonance (NMR), and infrared spectrochemical analysis (IR) confirmed it to be trimethylsiloxydiphenylchlorosilane with the following structural formula.

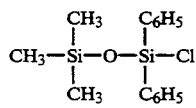

A solution containing 70 g (228.4 mmol) of the trimethylsiloxydiphenylchlorosilane described in the preceding section of this example and 200 mL of hexane was added dropwise to a stirred solution containing 24.0 g (285.5 mmol) of sodium bicarbonate and 250 mL water contained in a four-neck flask maintained at room temperature. Stirring was continued at 50° C. for an additional 8 hours following completion of the addition.

After a small quantity of crystalline solid by-product had been filtered off, the organic layer was separated from the aqueous layer of the filtrate, washed with water, and dried. Distillation of the solvent by heating under reduced pressure yielded 58.7 g of a colorless, transparent liquid. Analysis of the resultant colorless, transparent liquid by GLC, NMR, and IR confirmed it to be a mixture of two silicone compounds represented by structural formulas I and II. The yield of trimethylsiloxydiphenylsilanol was 86.4%, the overall yield was 61.7%, and the purity of the product was 96.9%.

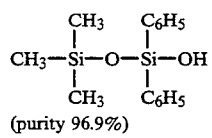

(purity 96.9%)

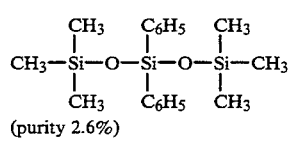

(purity 2.6%)

Example 2

A mixture of 61.5 g (542.8 mmol) of 90% pure dimethylvinylsilanol and 65.9 g (651.2 mmol) triethylamine was added dropwise with stirring to 164.8 g (651.2 mmol) diphenyldichlorosilane and 300 mL tetrahydrofuran contained in a four neck flask maintained at room temperature. Stirring at room temperature was continued for an additional hour following completion of addition, and the salt produced as a by-product was then removed by filtration. The filtrate was distilled under reduced pressure to yield 121.0 g (70% yield) of a colorless, transparent liquid that upon analysis by GLC, NMR, and IR was confirmed to be dimethylvinylsiloxydiphenylchlorosilane (III).

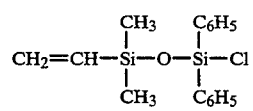

A solution containing 70 grams of III in 200 mL of hexane was added dropwise with stirring to a solution containing 24.0 g (285.5 mmol) sodium bicarbonate and 250 mL water in a four neck flask maintained at room temperature. Stirring was continued at 50° C. for an additional 8 hours following completion of addition. A small quantity of crystalline solid by-product was then filtered off, following which the organic layer was separated from the aqueous layer of the filtrate, washed with water, and dried. Distillation of the solvent by heating in vacuo yielded 60.5 g of a colorless, transparent liquid. Analysis of this colorless, transparent liquid by GLC, NMR, and IR confirmed it to be a mixture of organosilicon compounds IV and V. The yield of dimethylvinylsiloxydiphenylsilanol was 87.7%, its overall yield based on initial starting materials was 61.4%, and its purity was 95.5%.

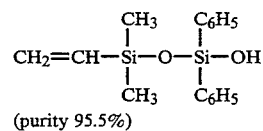

(purity 95.5%)

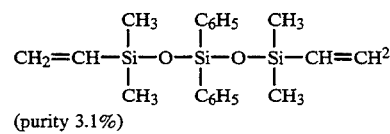

(purity 3.1%)

Comparison Example 1

The following ingredients were charged into a stirrer-equipped four-neck flask: 150 g (694.4 mmol) diphenylsilanediol, 29.6 g (291.7 mmol) triethylamine, 250 mL tetrahydrofuran, and 300 mL diethyl ether. The temperature of the contents of the flask was then reduced to −10° C. by ice water cooling, at which time 30.1 g (277.8 mmol) of trimethylchlorosilane were added dropwise. Stirring of the reaction mixture was continued for an additional 2.5 hours at room temperature following completion of the addition. The salt by-product was then filtered off and the solvent was distilled from the filtrate under reduced pressure at 60° C. The unreacted diphenylsilanediol was precipitated by the addition of 500 mL pentane to the residue and was separated by filtration. Distillation of the solvent in vacuo at 70° C. from the filtrate yielded 56.4 g of a colorless, transparent liquid. Analysis of the clear, colorless liquid by GLC, NMR, and IR confirmed it to be a mixture of the silicone compounds with structural formulas VI, VII and VIII. The yield of trimethylsiloxydiphenylsilanol was 59.2%, and its purity was 84.6%.

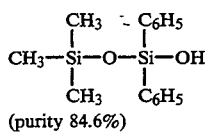

(purity 84.6%)    VI

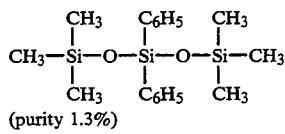

(purity 1.3%)    VII

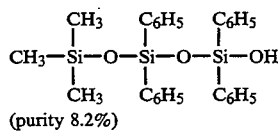

(purity 8.2%)    VIII

Comparison Example 2

The following ingredients were placed in a stirrer-equipped four-neck flask: 28.2 g (335.9 mmol) sodium bicarbonate and 150 mL water. A mixture of 15.9 g (98.8 mmol) hexamethyldisilazane, 50 g (197.6 mmol) diphenyldichlorosilane, and 100 g toluene was added dropwise at a rate that avoided exceeding a reaction temperature of 40° C. A large quantity of by-product in the form of white crystals (weight after drying=35.7 g) was filtered off, and the organic phase was separated from the aqueous phase of the filtrate, washed with water, and dried. The solvent was distilled off by heating in vacuo to afford yield 5.5 g of a clear, colorless liquid. The results of analysis by GLC, NMR, and IR confirmed this clear, colorless liquid to be a mixture of the organosilicon compounds IX, X, XI and XII. The yield of trimethylsiloxydiphenylsilanol was 6.1%, and its purity was 63.3%.

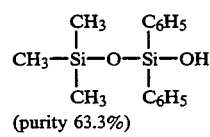

(purity 63.3%)    IX

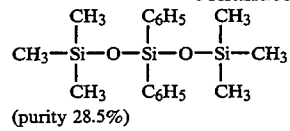

(purity 28.5%)    X

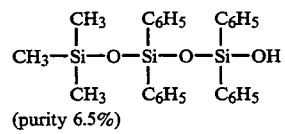

(purity 6.5%)    XI

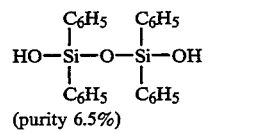

(purity 6.5%)    XII

Application Example 1

The following ingredients were combined, blended in a kneader type mixer, and finally heated in the mixer for 2 hours at 170° C. to yield a silicone rubber base: 100 weight parts trimethylsiloxy-terminated organopolysiloxane exhibiting an average degree of polymerization of 3,000 and containing 99.92 mol % dimethylsiloxane units and 0.18 mol% methylvinylsiloxane units, 32 weight parts dry-method silica with specific surface area of 300 m²/g, and 8.0 weight parts trimethylsiloxydiphenylsilanol prepared as described in Example 1. A heat curable silicone rubber composition of this invention (Sample 1) was prepared by the addition with mixing to homogeneity of 0.4 weight parts 2,5-dimethyl-2,5-di(tert-butylperoxy)hexane as the curing agent into 100 weight parts of the silicone rubber base.

This curable silicone rubber base was press-molded at 170° C./20 kg/cm² for 10 minutes to yield a molded silicone rubber sheet having a thickness of 2 mm. The sheet was then post cured for 4 hours in a circulation oven maintained at 200° C. The properties of the resultant sheet were measured, and these results are reported in Table 1. The storage stability of the uncured sheet was evaluated by storing the sheet for 4 weeks at loom temperature. The same type and amount peroxide used for Sample 1 was then blended into the composition, which was then cured under the same conditions described for Sample 1. Roll workability was again excellent. A portion of the cured molded sheet was also stored for 1 week at room temperature, and the surface evaluated for the presence or absence of white spots.

A silicone rubber molded sheet outside the scope of the present invention, referred to hereinafter as Comparative Sample 1, was also prepared as described for Sample 1, but using diphenylsilanediol in place of the trimethylsiloxydiphenyl-silanol. Table 1 reports the results from the evaluation of the resultant molded sheet as well as the results from the evaluation of the presence/absence of white spots on the surface of the molded sheet after it had been stored for 1 week at room temperature.

TABLE 1

| Plasticizer | | Sample 1 | Comparative Sample 1 |
| --- | --- | --- | --- |
| trimethylsiloxydiphenylsilanol | | 8.0 | 0.0 |
| diphenylsilanediol | | 0.0 | 8.0 |
| Physical Properties | | | |
| hardness | (JIS A) | 35 | 35 |
| tensile strength | (kgf/cm²) | 88 | 53 |
| tear strength | (kgf/cm) | 30 | 17 |

TABLE 1-continued

| Plasticizer | Sample 1 | Comparative Sample 1 |
|---|---|---|
| elongation (%) | 704 | 890 |
| presence/absence of white spots | absent | present |

That which is claimed is:

1. In a method for preparing a filled organosiloxane composition by blending a curable polyorganosiloxane with an inorganic filler in the presence of a plasticizer selected from the group consisting of organosilicon compounds containing at least one silanol group per molecule, the improvement comprising selecting said plasticizer from among triorganosiloxydiphenyl-silanols of the general formula

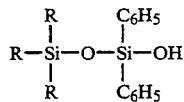

where $C_6H_5$ designates the phenyl radical and each R is individually selected from the group consisting of substituted and unsubstituted monovalent hydrocarbon radicals.

2. A method according to claim 1 where the concentration of said plasticizer is from 0.05 to 20 weight parts per 100 weight parts of said curable polyorganosiloxane.

3. A method according to claim 2 where said composition includes an amount of a curing agent sufficient to cure said polyorganosiloxane.

* * * * *